United States Patent [19]

Gilmore, Jr. et al.

[11] Patent Number: 5,263,925
[45] Date of Patent: Nov. 23, 1993

[54] PHOTOPHERESIS BLOOD TREATMENT

[76] Inventors: Thomas F. Gilmore, Jr., 5420 N. Ocean, Riviera Beach, Fla. 33404; Thomas F. Gilmore, III, 14370 68th Dr. North, Palm Beach Gardens, Fla. 33410

[21] Appl. No.: 734,165

[22] Filed: Jul. 22, 1991

[51] Int. Cl.⁵ .............................................. A61M 1/03
[52] U.S. Cl. ................................. 604/4; 604/6; 604/21
[58] Field of Search ..................... 604/4–6, 604/21; 128/690, 640, 798, 800–802

[56] References Cited

U.S. PATENT DOCUMENTS

| | | |
|---|---|---|
| 1,659,085 | 2/1928 | Cunningham et al. |
| 1,683,877 | 9/1928 | Edblom et al. |
| 2,357,238 | 8/1944 | Trimble |
| 4,321,919 | 3/1982 | Edelson |
| 4,398,906 | 8/1983 | Edelson ............... 604/6 |
| 4,428,744 | 1/1984 | Edelson |
| 4,464,166 | 8/1984 | Edelson |
| 4,568,328 | 2/1986 | King ...................... 604/6 |
| 4,612,007 | 9/1986 | Edelson |
| 4,684,521 | 8/1987 | Edelson |
| 4,822,335 | 4/1989 | Kawai et al. |
| 4,838,852 | 6/1989 | Edelson et al. |
| 4,860,743 | 8/1989 | Abela ..................... 604/15 |
| 4,878,891 | 11/1989 | Judy et al. |
| 4,897,789 | 1/1990 | King et al. ............. 604/4 X |
| 4,950,225 | 8/1990 | Davidner et al. ...... 604/4 |
| 4,955,857 | 9/1990 | Shettigar |
| 4,960,408 | 10/1990 | Klainer et al. |
| 5,007,427 | 4/1991 | Suzuki et al. ......... 128/659 |
| 5,010,896 | 4/1991 | Westbrook ............. 128/798 |
| 5,041,108 | 8/1991 | Fox et al. .............. 604/15 X |
| 5,078,134 | 1/1992 | Hillman et al. ........ 128/783 X |

FOREIGN PATENT DOCUMENTS

91/16945  11/1991  World Int. Prop. O. ............ 604/21

OTHER PUBLICATIONS

The New York Times Science Section of Oct. 23, 1990 pp. B5, B8 entitled: Light Can Unmask the Traitorous Cells of Immune Disease.

Scientific American Offprints, Jun. 1985, vol. 252, No. 6, pp. 46–53 entitled The Immunologic Function of Skin by Richard L. Edelson et al.

The New England Journal of Medicine, vol. 316, Feb. 5, 1987, No. 6 Richard Edelson et al entitled: Treatment of Cutaneous T-Cell Lymphoma by Extracorporeal Photochemotherapy.

Scientific American, Aug., 1988, vol. 256, No. 8 by Richard L. Edelson entitled Light-Activated Drugs.

The Yale Journal of Biology and Medicine, vol. 62, No. 6, Nov./Dec. 1989 pp. 565–577 by Richard L. Edelson, M. D. entitled: Photopheresis: A New Therapeutic Concept.

Yale University School of Medicine, New Haven, Conn. by Richard L. Edelson pp. 227–237 vol. 19 entitled: Treatment of Cutaneous T Cell Lymphoma.

Primary Examiner—Robert A. Hafer
Assistant Examiner—Sam Rimell
Attorney, Agent, or Firm—Hill, Steadman & Simpson

[57] ABSTRACT

A system for photopheresis treatment of immune diseases in the blood without immobilizing the patient or contacting the blood with treating agents, includes portable apparatus worn by the patient and a method of irradiating blood with rays as the blood flows continuously in a closed sterile loop path.

21 Claims, 3 Drawing Sheets

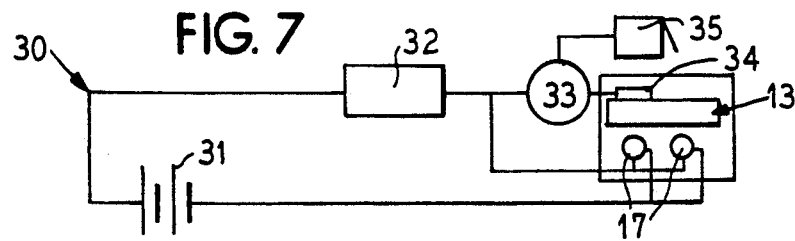
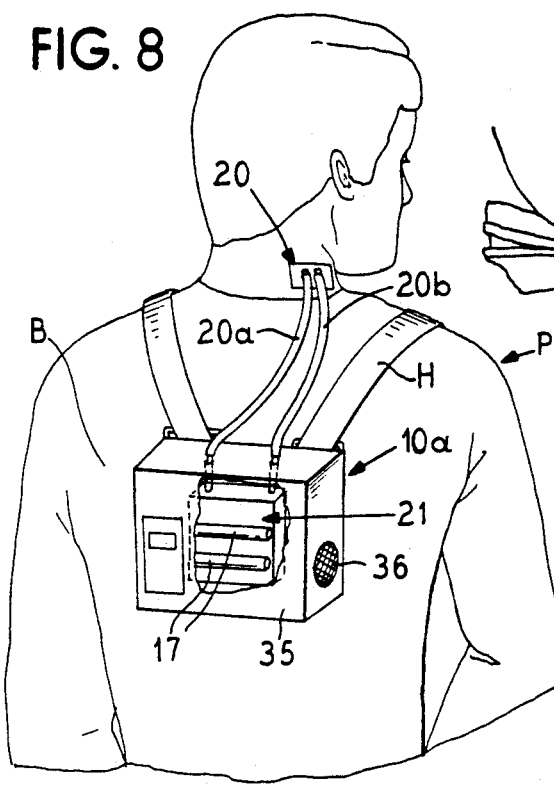
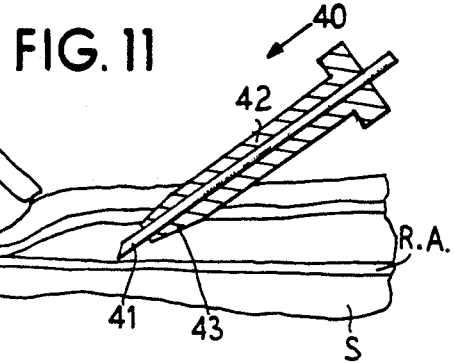
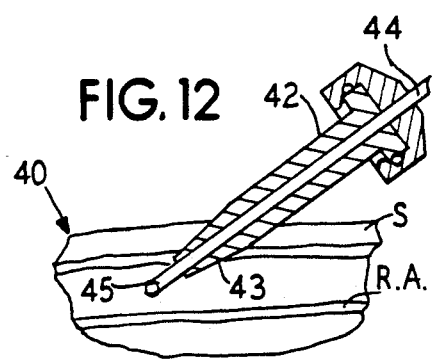
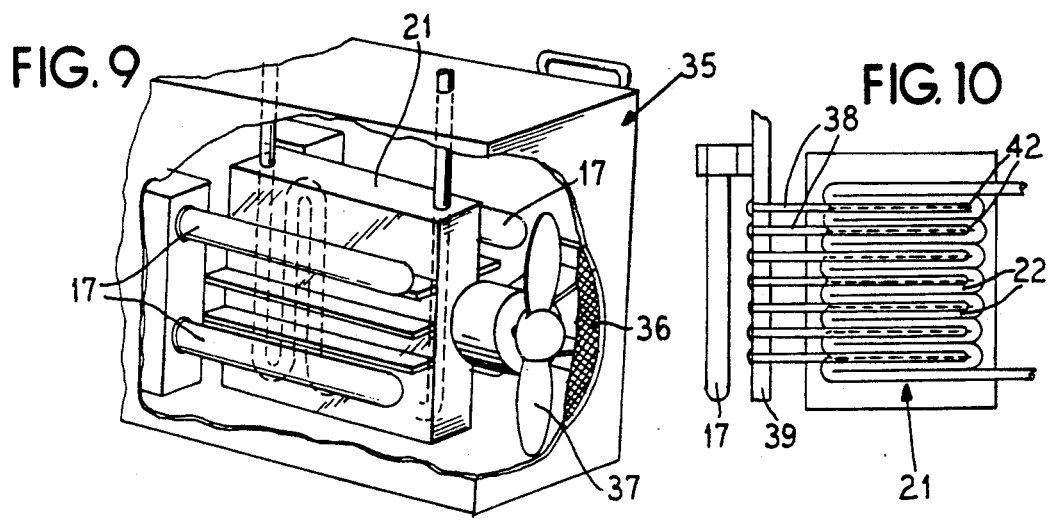

PHOTOPHERESIS BLOOD TREATMENT

BACKGROUND OF THE INVENTION

1. Field of the Invention

This invention relates to the art of photopheresis treatment of blood without inhibiting the mobility of the patient and more specifically deals with portable apparatus adapted to be worn by a patient which will irradiate blood as it flows between an artery and a vein and to a process of treating autoimmune diseases in a closed loop blood circulating system.

2. Description of the Prior Art

Heretofore photopheresis blood treatment has been extracorporeal and has required cumbersome apparatus which incapacitates the patient and contacts the blood with external treating agents. This type of treatment requires external power sources to energize pumps, ray emitting lamp bulbs, cooling devices and the like. Since the treatment is usually quite prolonged, the patient must undergo a somewhat traumatic dehabilitating experience in a treatment center such as a hospital and contacting the blood with external treating agents exposes the patient to infection and disease.

It would therefore be an improvement in this art to provide photopheresis blood treatment apparatus which is completely portable and can be worn by the patient to accommodate free unrestricted normal activities without discomfort.

It would be a further improvement in this art to provide continuous photopheresis treatment of blood in a closed sterile loop without contacting the blood with treating agents.

It would be a specific improvement in this art to eliminate heretofore required cumbersome equipment and blood contacting agents for photopheresis blood treatment.

SUMMARY OF THE INVENTION

According to this invention, photopheresis blood treatment is conducted without immobilizing the patient, interrupting the blood flow or contacting the blood with external agents.

In one form of the invention, there is provided a compact ray permeable cell adapted to be worn on the body of a patient and detachably connected to a cannula between an artery and a vein providing an elongated flow path exposed to rays from an adjacent emitter that is also worn by the patient. The emitter may be a battery energized tube or bulb discharging blood treating rays or beams such as an ultraviolet rays or laser beams effective to irradiate and cleanse the blood. The power source for the ray emitting bulbs is a battery also worn by the patient with sufficient capacity to activate the tubes or bulbs over a prolonged period. The rays from the bulbs can be transmitted to the cell through fiber optic strands.

In another form of the invention, the rays or beams are transmitted by fiber optics strands directly to the blood flowing through an artery or vein of the patient.

In a preferred cell embodiment, the cell is a flexible plate adapted to conform with the shape of the body part on which it is to be worn and having a very elongated serpentine flow path between its inlet and outlet to provide prolonged exposure of the blood to the rays as the blood flows therethrough.

In a preferred fiber optics embodiment one or more fiber optic strands transfer the rays or beams from the emitter to lens heads inserted directly in an artery or vein of the patient.

In the cell embodiments, reflectors are preferably provided to concentrate the rays on the cell. Low voltage ray emitting tubes are preferred to maintain body temperature of the blood. The serpentine blood flow path through the cell preferably has a very small diameter providing a capillary like exposure of the blood to the rays. The power supply for the rays emitting tubes or bulbs can conveniently be worn by a shoulder suspender or a conventional belt around the waist of the patient.

The transparent or ray permeable cell and the adjacent ray emitting tubes or bulbs can be carried by a loop and hook "Velcro" band conveniently strapped around the wrist or arm of the patient or secured over the back or chest at locations where a cannula can be conveniently inserted in adjacent arteries and veins. Straps can conveniently mount the cell and ray emitter at such locations.

The preferred ray emitter is a low voltage ultraviolet ray tube operating at room temperatures.

The preferred device also includes a light sensor of the type used in cameras for detecting a change in the color of the blood flowing through the cell. In the unlikely event of clogging of the blood to impede or stop flow through the cell, the blood color will darken to activate the sensor and set off an alarm.

The invention also preferably includes a timer on the power pack to shut off the current supply to the ray emitting tubes or bulbs after a predetermined period thereby preventing overexposure in the event the patient is asleep or fails to manually turn off the device.

Further in the unlikely event that the temperature of the blood is raised during treatment, cooling means are provided such as air circulating passages, heat radiating fins and the like for maintaining the blood at body temperature.

Preferred embodiments of the invention are illustrated in the accompanying drawings in which.

Figure 3:
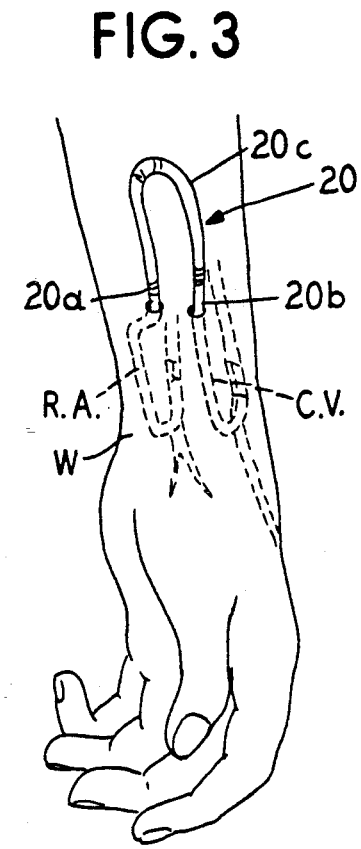

FIG. 3 is a perspective view illustrating an arterial cannula installed in the radial artery of a patient's wrist together with a venous cannula installed in the cerphalic vein adjacent the radial artery and connected to each other so that blood flows continuously through the tubes when the two cannulas are connected or through the cell of the apparatus when the cannulas are separated and connected to the inlet and outlet ports of the cell.

Figure 4:
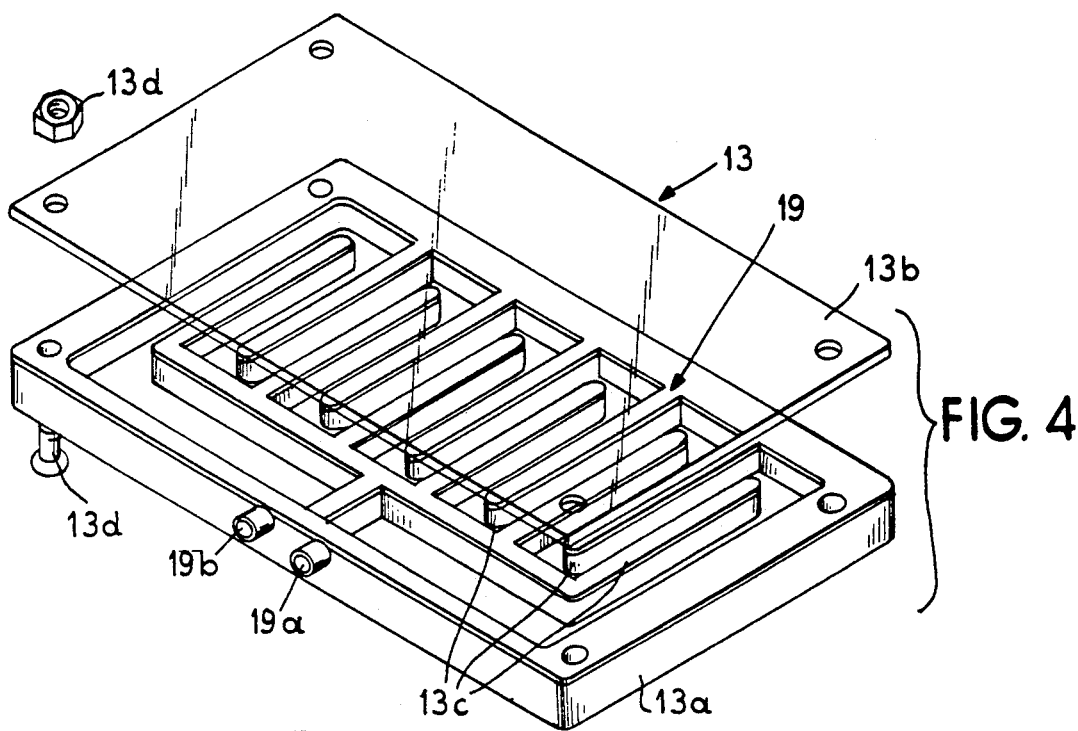

FIG. 4 is an exploded perspective view of a cell of the apparatus showing the serpentine flow through path for the blood.

Figure 5:
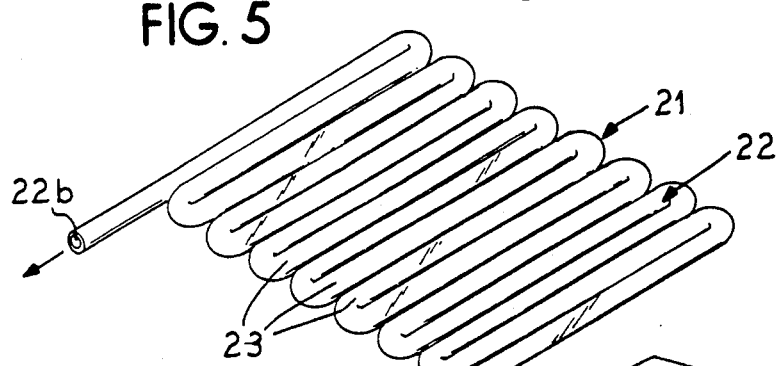

FIG. 5 is a perspective view of another embodiment of a cell for the apparatus.

Figure 2:
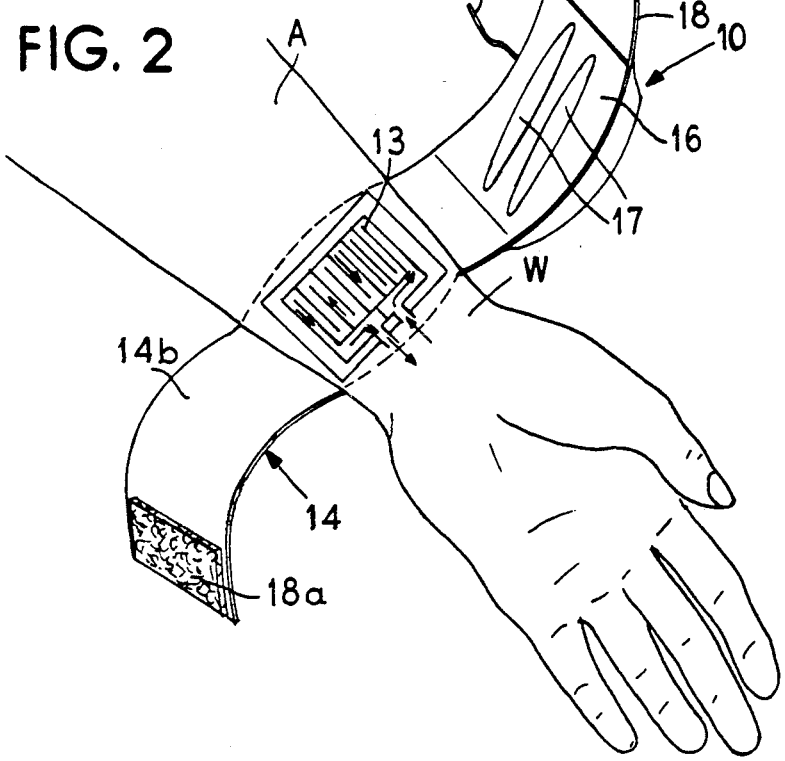
FIG. 2 is a perspective view of the apparatus of this invention illustrating the manner in which the ray emitter and the cell of the apparatus is incorporated in a bracelet or wristband type carrier wrapped around the wrist of the patient.
Figure 6:
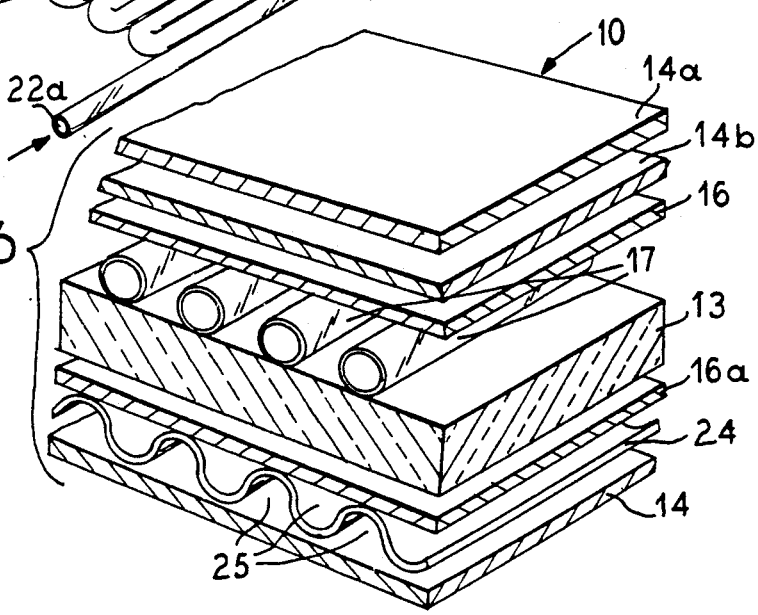

FIG. 6 is an exploded transverse sectional view through the wristband or bracelet type apparatus of FIG. 2 in closed position and showing air circulating passages to cool the cell.

FIG. 7 is a circuit diagram illustrating the manner in which the ray emitting tubes or bulbs are energized through a solid state invertor.

FIG. 8 is a schematic view of another embodiment of the invention worn on the back of the patient and partially broken away to show interior components.

FIG. 9 is a fragmentary perspective view, with parts broken away of FIG. 8 showing ray emitting bulbs on both sides of the cell and an air circulating fan to control temperature of the blood.

FIG. 10 is a schematic view of a capillary cell equipped with fiber optic strands delivering the rays from a ray emitter.

FIG. 11 is a schematic view showing a catheter being inserted in an artery.

FIG. 12 is a schematic view like FIG. 11.

BRIEF DESCRIPTION OF THE ILLUSTRATED PREFERRED EMBODIMENTS

Figure 1:
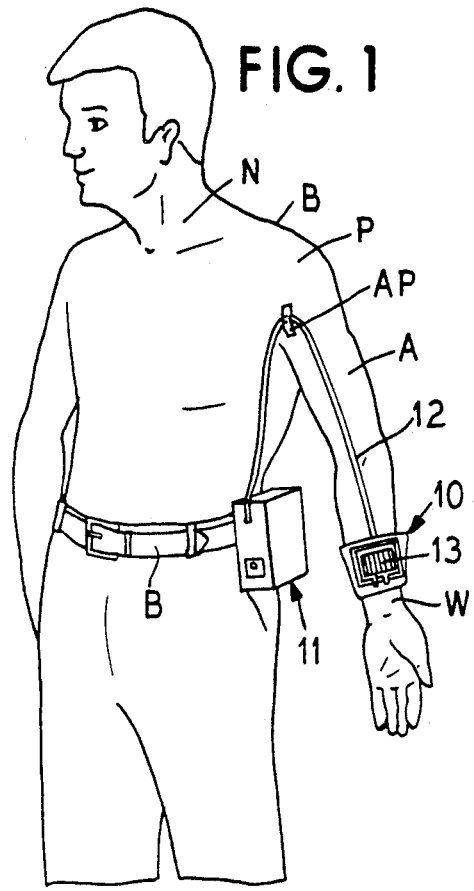
FIG. 1 is a schematic view of the apparatus of this invention worn on the wrist of a patient with a power supply pack carried on the wrist belt of the patient.

In FIG. 1, the cell apparatus 10 of this invention is illustrated as mounted on the wrist W of a patient P with the power pack 11 of the apparatus carried on the waist belt B of the patient P. The device 10 is connected to the power pack 11 through an electrical conduit wire 12 which can be conveniently laced through a shirt or coat sleeve over the arm A of the patient around the armpit AP and down to the belt area B.

It should be understood that the device 10 can be strapped around the upper portion of the arm A or can be secured to the neck area N or the back area B of the patient.

As illustrated in FIG. 2, the device 10 includes a ray permeable or transparent cell 13 placed on the inside of the patient's wrist W. A loop and hook "Velcro" strap 14 wrapped over the back of the patient's wrist has extended tabs 14a and 14b projecting from the back of the wrist. The portion 14a carries on its inner face, a reflective pad 16 with a pair of ultraviolet ray lamps 17 overlying the pad 16. The outer face of the portion 14a may have either the hook or loop surface 18 of the strap 14 while the portion 14b of the strap may have the complimentary loops or hooks 18a on its inner face for locking with the surface 18 of the tab portion 14a. The tab portion 14a is lapped over the cell 13 to align the tubes 17 with the cell and the tab portion 14b is then applied over the surface 18 of the tab portion 14a to hold the cell 13 and the lamps 17 over the inside of the wrist W.

As shown in FIG. 4 the cell 13 is a flat plate composed of an open top tray 13a closed by a lid 13b. The interior of the tray has a series of spaced parallel upstanding longitudinal baffles 13c with alternate opened and closed ends defining therebetween an extended length serpentine passageway 19, preferably of capillary dimensions, with an inlet port 19a and an outlet port 19b in a side end edge of the cell 13. Fasteners 13d at the corners of the cell secure the lid 13b to the tray 13a to seal the passageway 19.

The inlet and outlet ports 19a and 19b of the cell 13 are connected to a cannula 20 as shown in FIG. 3. The cannula 20 has as an arterial tube leg 20a inserted in the radial artery R.A. of the patient's wrist "W" and a vein tube leg 20b inserted in the adjacent cephalic vein. A removable tube section 20c connects the tube legs 20a and 20b. When the tube section 20c is in place, the blood flows freely in a closed loop from the artery to the vein. Then when the section 20c is removed and the tube legs 20 and 20b are connected to the inlet and outlet ports 19a and 19b of the cell 13, the blood also flows in a closed loop including the elongated passageway 19 through the cell 13. Therefore in the use, and also in the non-use positions of the cannula 20, the patient's blood is never contacted externally and the only input to the blood is from the rays or beams permeating the cell 12. Prior to treatment, the patient may ingest a known type of photoactive agent such as psoralin.

The cell 13 is preferably composed of the same type of plastics materials that are commonly used for the IV tubing in hospitals.

As shown in FIG. 5, a modified cell 21 is composed of a molded serpentine wound flat plate-like bundle of tubing 22 with the legs 23 of the tube secured together in side-by-side relation. The tube 22 is molded with an inlet end 22a and an outlet end 22b with the looped side by side legs 23 therebetween. These looped legs 23 legs are integrally connected in side-by-side relation providing a flexible plate-like cell. The internal diameter of the tubing 22 is preferably sufficiently small to provide a capillary flow path for the blood. The provision of a flexible cell 21 facilitates close wrapping of the apparatus around the selected body part for tapping the blood.

As demonstrated in the exploded view of FIG. 6, when the wristband type apparatus 10 of FIGS. 1 and 2 is closed around the arm A of the patient, the ray emitting tubes 17 overlie a face of the cell 13 and the reflector pad 16 overlies the tubes or bulbs 17. The leg 14a of the strap 14 overlies the leg 14b and the hook and hoop surfaces of these legs 14a and 14b interlock to hold the band tightly around the wrist. A second reflective pad 16a underlies the cell 13. A corrugated pad 24 underlies the pad 16a to provide air passages 25 between the corrugations which are effective to dissipate objectionable heat from the tubes 17 and prevent heating of the blood flowing through the cell above body temperatures. The strap 14 underlies the pad 24.

As illustrated in FIG. 7, the totally portable apparatus of this invention is activated in a very simple circuit 30 including a battery 31 which is preferably of the rechargeable type and a solid state invertor 32 activated by the battery 31 to energize the ray emitting lamps or bulbs 17. These ray emitters are preferably in the from of ultraviolet ray tubes operating on a low voltage to prevent heating. The circuit 30 includes a timer 33 that can be set to turn off the bulbs 17 after any desired treatment time and a photoelectric sensor 34 adjacent the cell 13 to detect discoloration of the blood flowing through the cell. The sensor will activate an alarm in the form of a buzzer 35 to show an unlikely increase in temperature of the blood or to turn off the bulbs 17.

As shown in FIG. 8, a modified apparatus 10a of this invention is illustrated in the form of a backpack 35 strapped to the back B of the patient P just below the shoulders by a harness H. A cell 21 of the type shown in FIGS. 4 or 5 is mounted inside of the backpack 35 and is connected by a cannula such as 20 of FIG. 3 which has the arterial leg portion 20a of the cannula inserted in the cartoid artery of the patient's neck with the leg portion 20b of the cannula inserted in the adjacent jugular vein. The blood flows through the cell 21 in the same manner illustrated in FIG. 5.

As shown in FIG. 9, the ray emitting tubes 17 are mounted in the backpack 35 on both sides of the cell 21. The backpack 35 has an air flow passage 36 therethrough and a fan 37 circulates air around the ray emitter tubes 17 to prevent heating of the blood as it circulates through the cell 21.

As illustrated in FIG. 10, in the event it becomes desirable to use ray emitters which operate at relatively high temperatures, the blood can be irradiated through a cell 21 positioned remote from the ray emitter tube 17 and the rays transmitted to the cell 21 through fiber optic strands 38 carried for example in a plate 39 adjacent the tubes 17. The strands 38 have elongated concave lenses 42 closely overlying the cell 21 and directing the rays along the looped serpentine passages 22.

In another embodiment 40 shown in FIGS. 11 and 12 the skin S overlying an artery such as R.A. of FIG. 3 is pierced by a needle 41 inserted into the artery through a catheter 42 while blood flow is stopped by depressing the artery above the needle as shown in FIG. 11. The tip 43 of the catheter is inserted in the artery, the needle 41 is withdrawn and a fiber optic strand 44 is inserted through the catheter to position a convex lens 45 on the end of the strand in the bloodstream. The strand 44 receives rays from an emitter 17 as illustrated in FIG. 10 and the blood is directly irradiated as it flows through the artery.

From the above descriptions and the illustrations in the drawings it will be understood that the invention provides photopheresis blood treatment without immobilizing the patient or exposing the blood to outside agents or interrupting the blood flow.

It will be understood by those skilled in this art that many variations and modifications of the preferred embodiments herein described and illustrated can be made without departing from the scope of this invention.

We claim as our invention:

1. A portable photopheresis blood treatment apparatus adapted to be worn by a patient without immobilizing the patient's activities which comprises a portable ray emitter, means for removably mounting the emitter on the body of a patient, a portable power pack for energizing the emitter, means for removably mounting the power pack on the body of a patient, and a ray permeable cell having an elongated serpentine path therethrough with an inlet receiving blood from an artery of the patient and an outlet discharging to a vein of the patient removably mounted on the body of the patient for directing rays from the emitter into the bloodstream of the patient.

2. A photopheresis blood treatment apparatus adapted to be comfortably worn by a patient undergoing treatment without impeding the patient's activities which comprises a ray emitter, a ray permeable cell having an elongated blood flow path, a cannula for flowing the patient's blood directly from an artery to a vein continuously through said path without exposing the blood to external agents, means for directing rays from the emitter to the cell to irradiate the blood flowing therethrough, means for removably mounting the emitter and cell on the body of the patient to be treated, means for energizing the emitter, and means for removably mounting said energizing means on the body of the patient.

3. Apparatus for photopheresis treatment which comprises a portable ray emitter, a portable power pack for energizing said emitter, a catheter insertable into the bloodstream of a patient, a fiber optic strand having a trailing end and a leading end, said trailing end of the strand receiving rays from the emitter, a lens on said leading end of said strand held by said catheter to direct rays from the strand into the bloodstream, and means for mounting the emitter and power pack on the body of the patient.

4. The method of irradiating a patient's blood without exposing the blood which comprises ingesting a photo active agent into the patient for photoactivating the blood, continuously flowing the patient's blood containing the photoactive agent between an artery of the patient, through an elongated passage of a ray permeable cell carried by the body, and returning to the vein of the patient and directing blood treating rays from an emitter to the cell.

5. The method of treating autoimmune diseases in a patient's blood without exposing the blood to external apparatus which comprises injecting a photo active agent into the patient to photoactivate the blood, injecting the lens end of a fiber optic strand into the bloodstream of the patient without blocking the blood flow, directing blood treating rays through the strand to activate the lens, and directing the blood treating rays from the activated lens into the blood to irradiate the blood.

6. The apparatus of claim 1 wherein the ray emitter is a bulb mounted adjacent said cell.

7. The apparatus of claim 1, wherein the power pack includes a rechargeable battery.

8. The apparatus of claim 1 including means adjacent the cell for maintaining the bloodstream at body temperature.

9. The apparatus of claim 1, wherein the means for directing rays from the emitter is a fiber optic strand means.

10. The apparatus of claim 2, wherein the flow path through the cell is serpentine and the material of the cell is an inert transparent plastics material.

11. The apparatus of claim 2, including a band for strapping the cell and emitter on a portion of the arm of the patient.

12. The apparatus of claim 11, wherein the band has hook and loop fasteners to close the band and hold the cell and emitter firmly against the arm.

13. The apparatus of claim 2, including means circulating air around the cell for cooling the blood as it flows through the cell.

14. The apparatus of claim 3, wherein the catheter has a path therethrough selectively receiving a skin piercing needle and a fiber optic strand.

15. The apparatus of claim 3, wherein the fiber optic strand has a convex lens on the end thereof.

16. The apparatus of claim 9, wherein the fiber optic strand means has an elongated concave lens overlying the cell.

17. The method of claim 4, including the step of flowing the blood through an elongated serpentine capillary passage of the cell.

18. The method of treating autoimmune diseases in blood containing a photoactive agent without exposing the blood to external apparatus which comprises injecting the lens end of a fiber optic strand into a radial artery of the wrist of a patient, and directing blood treating rays through the strand to activate the lens to direct the rays to irradiate the blood.

19. The method of photopheresis blood treatment which comprises continuously flowing blood containing a photoactive agent between the radial artery of the patient's wrist, through an elongated passage of a ray permeable cell carried by the body, and returning to the cephalic vein of the patient's wrist, and directing blood treating rays from an emitter to the cell to irradiate the blood flowing therethrough.

20. The method of claim 4, wherein the blood containing the photoactive agent flows between the radial artery of the patient's wrist and the adjacent cephalic vein.

21. The method of claim 4, wherein the blood containing the photoactive agent flows between the cartoid artery of the patient's neck and the adjacent jugular vein of the patient.

* * * * *